US011051699B2

(12) United States Patent
Davis et al.

(10) Patent No.: US 11,051,699 B2
(45) Date of Patent: Jul. 6, 2021

(54) METHOD AND SYSTEM FOR ESTIMATING FRACTIONAL FAT CONTENT OF AN OBJECT OF INTEREST

(71) Applicant: ENDRA Life Sciences Inc., Ann Arbor, MI (US)

(72) Inventors: Christopher Nelson Davis, Ann Arbor, MI (US); Jang Hwan Cho, Ann Arbor, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 414 days.

(21) Appl. No.: 16/231,895

(22) Filed: Dec. 24, 2018

(65) Prior Publication Data

US 2020/0196872 A1  Jun. 25, 2020

(51) Int. Cl.
*A61B 5/00* (2006.01)
*A61B 5/20* (2006.01)

(52) U.S. Cl.
CPC ............ *A61B 5/0093* (2013.01); *A61B 5/201* (2013.01); *A61B 5/4244* (2013.01); *A61B 5/489* (2013.01); *A61B 5/4872* (2013.01); *A61B 5/7235* (2013.01); *A61B 5/7278* (2013.01); *A61B 2576/02* (2013.01)

(58) Field of Classification Search
CPC ..... A61B 5/0093; A61B 5/4872; A61B 5/489; A61B 5/4224; A61B 5/7235; A61B 5/7278; A61B 5/201; A61B 2576/02; A61B 8/5261; A61B 8/00; A61B 8/5223
See application file for complete search history.

(56) References Cited

U.S. PATENT DOCUMENTS

| 9,888,879 | B1  |   | 2/2018  | Cho et al. |           |
|-----------|-----|---|---------|------------|-----------|
| 9,888,880 | B1  | * | 2/2018  | Cho        | G16H 50/30 |
| 9,980,677 | B1  | * | 5/2018  | Cho        | A61B 8/5223 |
| 2017/0351836 | A1 | * | 12/2017 | Thornton  | A61B 5/4872 |

OTHER PUBLICATIONS

Lee Young; PCT International Search Report and Written Opinion; dated Apr. 24, 2020; 13 pages total; WIPO; Alexandria, VA, United States.

* cited by examiner

*Primary Examiner* — Peter Luong
(74) *Attorney, Agent, or Firm* — Stanley E. Jelic

(57) ABSTRACT

A method and system for estimating fractional fat content of an object of interest. The method and system include a thermoacoustic imaging system comprising an adjustable radio frequency (RF) applicator configured to emit RF energy pulses into the region of interest and heat tissue therein and an acoustic receiver configured to receive bipolar acoustic signals generated in response to heating of tissue in the region of interest; and one or more processors. The one or more processors are able to process bipolar acoustic signals received by the acoustic receiver in response to RF energy pulses emitted into the region of interest using the RF applicator to determine a setting for the RF applicator that yields bipolar acoustic signals with at least one enhanced metric thereof, determine an impedance of the RF applicator used to yield acoustic bipolar signals with the enhanced at least one metric, and estimate fractional fat content of the object of interest using the determined impedance.

20 Claims, 11 Drawing Sheets

METHOD AND SYSTEM FOR ESTIMATING FRACTIONAL FAT CONTENT OF AN OBJECT OF INTEREST

FIELD

The subject disclosure relates to thermoacoustic imaging and in particular, to a method and system for estimating fractional fat content of an object of interest.

BACKGROUND

Hepatic steatosis, also known as a fatty liver disease, is a condition where hepatocytes suffer from abnormal intracellular accumulation of fat, mostly in the form of triglycerides (TG). The two main types of hepatic steatosis are alcoholic liver disease (ALD) and non-alcoholic fatty liver disease (NAFLD). NAFLD is the most common cause of chronic liver disease in the United States. Hepatic steatosis can lead to progressive hepatic disease and is a risk factor for cardiovascular disease and diabetes. Liver biopsy with histologic analysis is commonly used for diagnosing and grading a fatty liver. However, due to the invasive nature of liver biopsy with histologic analysis and limitations such as lack of representation of the entire liver, non-invasive assessments based on cross-sectional imaging are being investigated.

Ultrasound imaging has been used for evaluating hepatic steatosis. Ultrasound imaging uses sound waves with frequencies higher than those audible to humans (>20 000 Hz). These sound waves are pulsed into tissue using a probe. The sound waves echo off the tissue. Different tissues reflect different degrees of sound. These echoes are analyzed through signal processing and are further processed using clinical ultrasound reconstruction algorithms to reconstruct ultrasound images for presentation and interpretation by an operator. Many different types of images can be reconstructed using ultrasound imaging. One such type is a B-mode image which displays the acoustic impedance of a two-dimensional cross-section of tissue. Ultrasound imaging, however, suffers from poor repeatability and reproducibility in evaluating hepatic steatosis.

Unenhanced computed tomography (CT) has been used for evaluating hepatic steatosis. Using unenhanced CT, fatty liver can be diagnosed based on its attenuation value and relative relationship with the spleen and blood. However, the sensitivity of unenhanced CT is limited.

Magnetic resonance imaging (MRI) has been used as a non-invasive imaging modality for diagnosing and quantifying hepatic steatosis. MRI data can be processed to estimate proton density fat fraction (PDFF) as a measure of fractional fat content. However, MRI is expensive.

Thermoacoustic imaging is an imaging modality that provides information relating to the thermoelastic properties of tissue. Thermoacoustic imaging uses short pulses of electromagnetic energy, such as radio frequency (RF) pulses, directed into a subject to heat absorbing features within the subject rapidly, which in turn induces acoustic pressure waves that are detected using acoustic receivers such as one or more thermoacoustic transducer arrays. The detected acoustic pressure waves are analyzed through signal processing, and processed for presentation as thermoacoustic images that can be interpreted by an operator.

Thermoacoustic imaging can be used to contrast fat or fatty tissues with soft or lean tissues due to their lower electrical conductivity and permittivity in RF compared to other water and ion-rich soft or lean tissues. Fat and fatty tissues also have a lower absorption coefficient compared to soft tissues like muscle. As such, thermoacoustic images provide a strong contrast between fat and fatty tissues and soft tissues like muscle.

Although techniques for detecting and grading hepatic steatosis have been considered, improvements are desired. It is therefore an object at least to provide a novel a method and system for estimating fractional fat content of an object using thermoacoustic imaging.

SUMMARY

It should be appreciated that this summary is provided to introduce a selection of concepts in a simplified form that are further described below in the detailed description. This summary is not intended to be used to limit the scope of the claimed subject matter.

Accordingly, in one aspect there is provided a method for estimating fractional fat content of an object of interest, the method comprising (i) directing, using a radio frequency (RF) applicator, one or more RF energy pulses into a region of interest, the region of interest comprising the object of interest and at least one reference that are separated by at least one boundary; (ii) detecting, using an acoustic receiver, at least one bipolar acoustic signal generated in the region of interest in response to the RF energy pulses and processing the at least one bipolar acoustic signal to determine a peak-to-peak amplitude thereof; (iii) adjusting an impedance of the RF applicator to enhance at least one metric of bipolar acoustic signals generated in the region of interest in response to RF energy pulses generated by the adjusted RF applicator; and (iv) estimating fractional fat content of the object of interest based on the adjusted impedance of the RF applicator.

In one or more embodiments, the at least one metric is at least one of the peak-to-peak amplitude of the bipolar acoustic signals, a maximum amplitude of the bipolar acoustic signals and an envelope of the bipolar acoustic signals.

In one or more embodiments, adjusting the impedance of the RF applicator to enhance at least one metric of bipolar acoustic signals comprises adjusting the impedance of the RF applicator to maximize the at least one metric of the bipolar acoustic signals.

In one or more embodiments, during step (i), the RF applicator is set at a predefined impedance.

In one or more embodiments, estimating fractional fat content of the object of interest based on the adjusted impedance of the RF applicator comprises comparing the adjusted impedance to the predefined impedance.

In one or more embodiments, estimating fractional fat content of the object of interest comprises looking up the adjusted impedance in a lookup table.

In one or more embodiments, adjusting the impedance of the RF applicator comprises at least one of adjusting a tuning element of the RF applicator; adjusting a volume of a waveguide of the RF applicator; and adjusting a temperature within the waveguide of the RF applicator.

In one or more embodiments, the boundary is at a location between at least two different types of tissue. The two different types of tissue may for example be one of: muscle and fat; a blood vessel and fat; and liver tissue and kidney tissue.

According to another aspect there is provided a system for estimating fractional fat content of an object of interest within a region of interest, the system comprising a thermoacoustic imaging system comprising an adjustable radio frequency (RF) applicator configured to emit RF energy pulses into the region of interest and heat tissue therein and an acoustic receiver configured to receive bipolar acoustic signals generated in response to heating of tissue in the region of interest; and one or more processors configured to process bipolar acoustic signals received by the acoustic receiver in response to RF energy pulses emitted into the region of interest using the RF applicator to determine a setting for the RF applicator that yields bipolar acoustic signals with at least one enhanced metric thereof; determine an impedance of the RF applicator used to yield acoustic bipolar signals with the enhanced at least one metric; and estimate fractional fat content of the object of interest using the determined impedance.

In one or more embodiments, the at least one metric is at least one of the peak-to-peak amplitude of the bipolar acoustic signals, a maximum amplitude of the bipolar acoustic signals and an envelope of the bipolar acoustic signals.

In one or more embodiments, the setting for the RF applicator is a setting that yields bipolar acoustic signals with at least one maximum metric thereof.

In one or more embodiments, the one or more processors are further configured to estimate the fractional fat content of the object of interest using a lookup table.

In one or more embodiments, the adjustable RF applicator comprises at least one tuning element configured to alter the impedance of a waveguide of the RF applicator.

In one or more embodiments, the at least one tuning element is rotatable to alter an impedance of the waveguide.

In one or more embodiments, the at least one tuning element produces audible clicks during rotation.

In one or more embodiments, each audible click is used to estimate the fractional fat content of the object of interest.

In one or more embodiments, the adjustable RF applicator comprises at waveguide having an adjustable volume.

In one or more embodiments, the adjustable RF applicator comprises at least one heating element configured to alter a temperature within a waveguide of the RF applicator.

According to another aspect there is provided an adjustable radio frequency applicator comprising a waveguide; at least one radio frequency (RF) emitter positioned within the waveguide and configured to generate RF energy pulses, the waveguide configured to direct generated RF pulses towards a region of interest; and at least one adjustable feature configured to manipulate a characteristic of the waveguide to adjust an impedance of the RF applicator.

According to another aspect there is provided a method for estimating fractional fat content of an object of interest, the method comprising (i) directing, using a radio frequency (RF) applicator, one or more RF energy pulses into a region of interest, the region of interest comprising the object of interest and at least one reference that are separated by at least one boundary; (ii) detecting, using an acoustic receiver, at least one bipolar acoustic signal generated in the region of interest in response to the RF energy pulses and processing the at least one bipolar acoustic signal to determine a peak-to-peak amplitude thereof; (iii) adjusting an impedance of the RF applicator; (iv) directing, using the adjusted RF applicator, one or more RF energy pulses into the region of interest; (v) detecting, using the acoustic receiver, at least one bipolar acoustic signal generated in the region of interest in response to the RF energy pulses generated by the adjusted RF applicator and processing the at least one bipolar acoustic signal to determine a peak-to-peak amplitude thereof; (vi) comparing the peak-to-peak amplitude determined at step (v) with a previously determined peak-to-peak amplitude; (v) repeating steps (iii), (iv) and (v) until the peak-to-peak amplitude of the at least bipolar acoustic signal determined at step (v) is maximized and; (vi) estimating fractional fat content of the object of interest based on the impedance of the RF applicator used to maximize the bipolar acoustic signal.

According to another aspect there is provided a method for estimating fraction fat content of an object of interest, the method comprising directing, using a radio frequency (RF) applicator, one or more RF energy pulses through at least one intermediate area and into a region of that comprises the object of interest, the one or more RF energy pulses having a known frequency and a known amplitude; utilizing a first power monitor to measure a forward power of the RF energy pulses; utilizing a second power monitor to measure a reflected power of the RF energy pulses; and estimating fractional fat content of the object of interest based on the forward power, the reflected power, and an estimated thickness of said at least one intermediate area.

According to another aspect there is provided a system for estimating fractional fat content of an object of interest, the system comprising a thermoacoustic imaging system comprising a radio frequency (RF) applicator configured to emit RF energy pulses through an intermediate area and into a region of interest comprising an object of interest and heat tissue therein; a first power monitor configured to measure a forward power of the RF energy pulses; a second power monitor configured to measure a reflected power of the RF energy pulses; and one or more processors configured to: estimate fractional fat content of the object of interest based on the measured forward power, the measured reflected power, and an estimated thickness of said at least one intermediate area.

BRIEF DESCRIPTION OF THE DRAWINGS

Embodiments will now be described more fully with reference to the accompanying drawings in which.

DETAILED DESCRIPTION OF THE EMBODIMENTS

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

In the following, a method and system for estimating fractional fat content of an object of interest are described. Generally, the method and system utilize an RF applicator to direct one or more RF energy pulses into a region of interest. Thermoacoustic data in the form of a bipolar acoustic signal is detected using an acoustic receiver. The impedance of the RF applicator is adjusted to enhance at least one metric of bipolar acoustic signals generated in the region of interest. Fractional fat content of an object of interest within the region of interest is estimated based on the adjusted impedance of the RF energy pulses.

Figure 1:
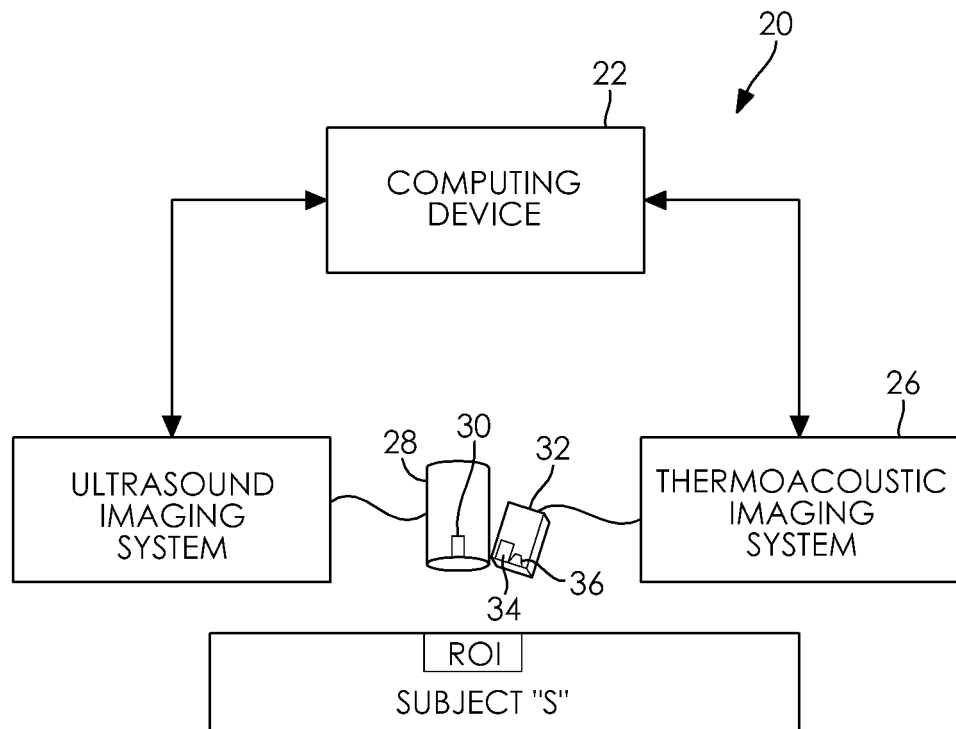
FIG. 1 is a schematic view of an imaging system.
Figure 2:
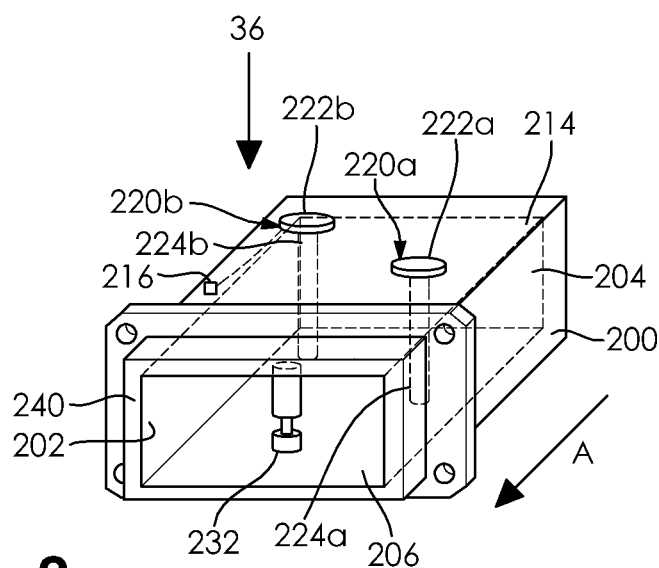
FIG. 2 is a perspective view of a radio frequency (RF) applicator forming part of the imaging system of FIG. 1.
Figure 2A:
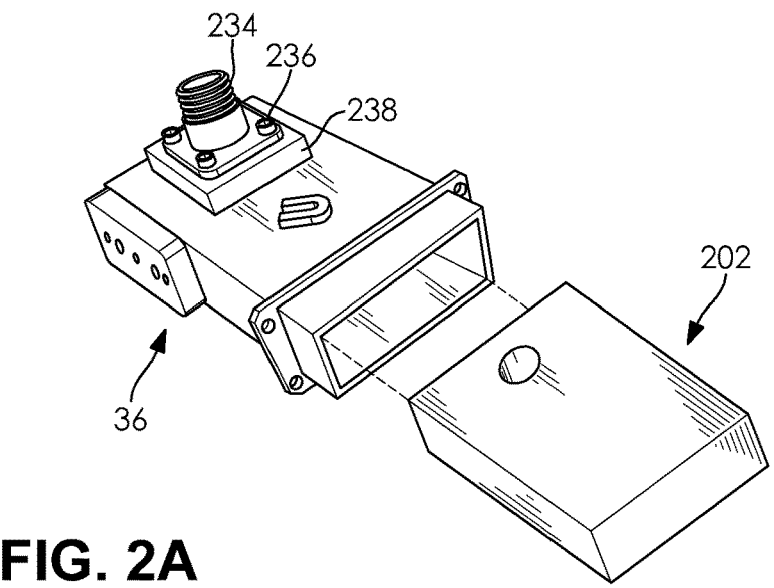
FIG. 2A is an exploded view of the RF applicator of FIG. 2 with an insert removed.
Figure 3:
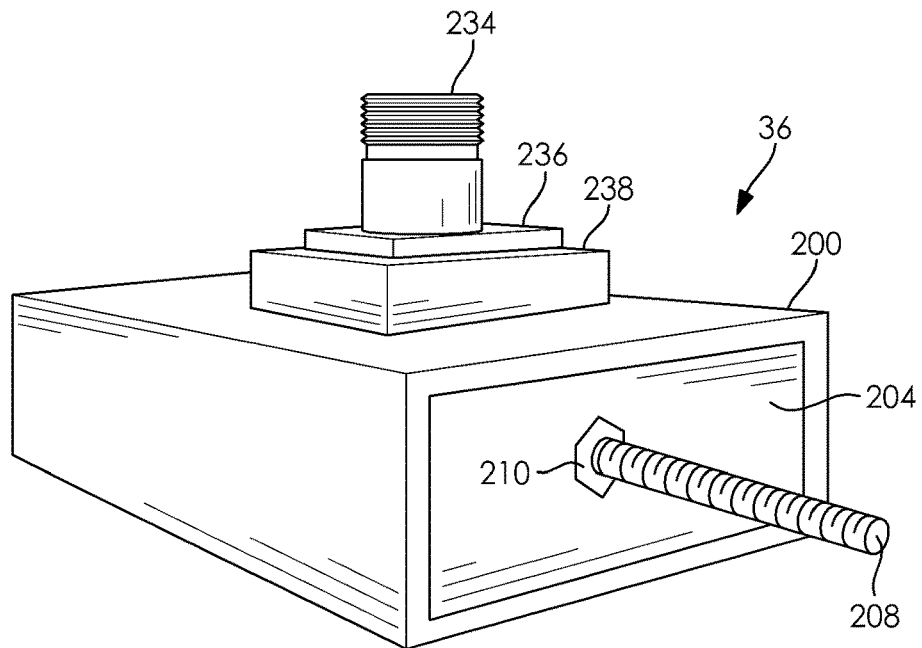
FIG. 3 is another perspective view of the RF applicator of FIG. 2.
Figure 3A:
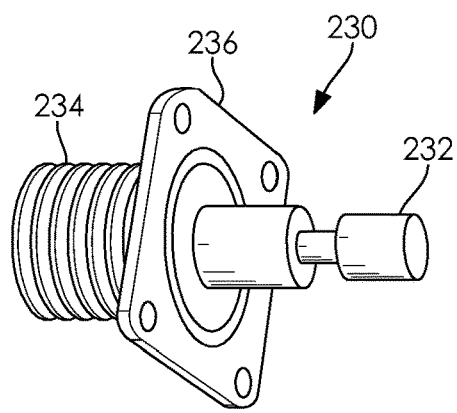
FIG. 3A is a perspective view of an RF source forming part of the RF applicator of FIGS. 2 and 3.

Turning now to FIG. 1, an exemplary imaging system is shown and is generally identified by reference numeral 20. As can be seen, the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a region of interest ROI associated with a subject S.

The programmed computing device 22 in this embodiment is a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26.

The ultrasound imaging system 24 comprises an acoustic receiver in the form of an ultrasound transducer 28 that houses one or more ultrasound transducer arrays 30 configured to emit sound waves into the region of interest ROI of the subject S. The sound waves directed into the region of interest ROI of the subject echo off tissue within the region of interest ROI, with different tissues reflecting varying degrees of sound. Echoes that are received by the one or more ultrasound transducer arrays 30 are processed by the ultrasound imaging system 24 before being communicated as ultrasound image data to the computing device 22 for further processing and for presentation as ultrasound images that can be interpreted by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described further herein.

The thermoacoustic imaging system 26 comprises an acoustic receiver in the form of a thermoacoustic transducer 32. The thermoacoustic transducer 32 houses one or more thermoacoustic transducer arrays 34 as well as a radio frequency (RF) applicator 36. It will however be appreciated that the RF applicator 36 may be housed separately from the thermoacoustic transducer 32. The RF applicator 36 is configured to emit short pulses of RF energy that are directed into tissue within the region of interest ROI of the subject. In this embodiment, the RF applicator 36 has a frequency between about 10 Mhz and 100 GHz and has a pulse duration between about 0.1 nanoseconds and 10 nanoseconds. The RF energy pulses delivered to the tissue within the region of interest ROI heat the tissue thereby to induce acoustic pressure waves that are detected by the thermoacoustic transducer 32. The acoustic pressure waves that are detected by the thermoacoustic transducer 32 are processed and communicated as thermoacoustic image data to the computing device 22 for further processing and for presentation as thermoacoustic images that can be interpreted by the operator.

In this embodiment, the ultrasound transducer 28 and thermoacoustic transducer 32 are mechanically interconnected so that the spatial relationship between the one or more ultrasound transducer arrays 30, the one or more thermoacoustic arrays 34 and the RF applicator 36 are known. The spatial relationship is set using a centerline of the one or more ultrasound transducer arrays 34, the one or more thermoacoustic transducer arrays 34, and RF applicator 36. Each centerline is defined as being a mid-point of an area of the respective transducer array.

In this embodiment, the spatial relationship between the one or more ultrasound transducer arrays 30 and the one or more thermoacoustic transducer arrays 34 is such that the centerline of the one or more thermoacoustic transducer arrays 34 is set at know angle $\alpha$ with respect to the centerline (also known as the axial axis or ultrasound transducer array beam axis) of the one or more ultrasound transducer arrays 30. The spatial relationship between the one or more thermoacoustic transducer arrays 34 and the RF applicator 36 is such that the centerline of the RF applicator 36 is spaced-apart and generally parallel to the centerline of the one or more thermoacoustic transducer arrays 34.

The imaging system 20 utilizes the known spatial relationship between the one or more ultrasound transducer arrays 30 and the one or more thermoacoustic transducer arrays 34 to increase the precision and accuracy of thermoacoustic imaging.

The coordinate system of the one or more ultrasound transducer arrays 30 of the ultrasound transducer 28 and the coordinate system of the one or more thermoacoustic transducer arrays 34 of the thermoacoustic transducer 32 are mapped by the computing device 22 so that acquired ultrasound and thermoacoustic images can be registered. Alternatively, the thermoacoustic imaging system 26 may make use of the one or more ultrasound transducer arrays 30 of the ultrasound transducer 28 by disconnecting the one or more ultrasound transducer arrays 30 from the ultrasound transducer 28 and connecting the one or more ultrasound transducer arrays 30 to the thermoacoustic transducer 32. As will be appreciated, by doing this coordinate mapping between the one or more ultrasound transducer arrays 28 and the one or more thermoacoustic transducer arrays 34 is not required.

Turning now to FIGS. 2, 2A, 3 and 3A, the RF applicator 36 is better illustrated. As can be seen, the RF applicator 36 comprises a hollow, generally rectangular, open-ended housing 200 formed of electrically conductive material. An insert 202 formed of ceramic or other suitable material lines the interior surface of the housing 200. An adjustable backplane 204 is positioned within the insert 202 adjacent one end of the housing 200. The adjustable backplane 204 closes one end of the insert 202 to define a partially enclosed space 206 within the insert 202. In this embodiment, the backplane 204 has a hole therein through which a threaded rod 208 extends. A nut 210 that is affixed to the external major surface of the backplane 204 threadably engages the threaded rod 208. Rotation of the threaded rod 208 causes the nut 210 to travel along the threaded rod 208 and hence, causes the backplane 204 to travel longitudinally within the insert 202. Depending on the direction of rotation of the threaded rod 208, the backplane 204 can be advanced into or out of the insert 202 allowing the volume of the partially enclosed space 206 to be adjusted. Although not shown, a handle may be provided on the threaded rod 208 to facilitate rotation thereof.

A heating element 214 and a temperature sensor 216 are accommodated in the space between the outer and inner surfaces of the housing 200. The temperature sensor 216 is configured to communicate temperature data to the computing device 22 indicating the temperature within the partially enclosed space 206 of the insert 202. The heating element 208 is configured to receive control signals from the computing device 22 and is energized when the temperature within the partially enclosed space 206 falls below a set threshold. In this manner, the temperature within the partially enclosed space 206 can be effectively controlled by the computing device 22 by comparing the temperature data received from the temperature sensor 216 with the set temperature and energizing the heating element 214 when needed.

In this embodiment, the heating element 214 extends along a lengthwise edge of the insert 202. Those of skill in the art will however appreciate that variations are possible. The heating element 214 may of course be positioned within the space between the outer and inner surfaces of the housing 200 at alternative locations. Furthermore, multiple heating elements 214 at various positions in the space between the outer and inner surfaces of the housing 200 may be employed. In this embodiment, the temperature sensor 216 is positioned adjacent a lengthwise edge of the insert 202 opposite the heating element 214. The temperature sensor 216 may of course be positioned in the space between the outer and inner surfaces of the housing 200 at alternative locations. Furthermore, multiple temperature sensors 216 at various positions in the space between the outer and inner surfaces of the housing 200 may be employed.

In this embodiment, the RF applicator 36 further comprises a plurality of tuning elements 220a and 220b that are laterally and longitudinally spaced along the housing 200. Tuning element 220a is generally centered along the housing 200 and comprises a head 222a and a threaded rod 224a extending therefrom. Tuning element 220b is to one side and behind the tuning element 220a in the view of FIG. 2 and comprises a head 222b and a threaded rod 224b extending therefrom. The heads 222a and 222b of the tuning elements are in the form of discs and are positioned external of the housing 200 adjacent one of its major surfaces. The threaded rods 222a and 222b of the tuning elements pass through threaded holes in the housing 200 that are aligned with holes in the insert 202 and extend into the partially enclosed space 206 of the insert 202. Each tuning element 220a, 220b is adjustable by rotating the respective head of the tuning element in a clockwise or counter-clockwise direction to increase or decrease the extent into which the threaded rod extends into the partially enclosed space 206. Although two tuning elements are shown, those of skill in the art will appreciate that the RF applicator 36 may comprise a single tuning element of more than two tuning elements.

An RF source 230 having an RF emitter 232 at one end that is configured to generate RF energy pulses, extends through aligned holes in the housing 200 and insert 202 so that the RF emitter 232 is suspended within the partially enclosed space 206 of the insert 202. The RF source 230 further comprises a threaded connector 234 to which control electronics are connected and a flange 236 that overlies a plinth 238 formed on the housing 200 and through which threaded fasteners pass and engage the plinth 238 thereby to secure the RF source 230 to the housing 200.

A window 240 is positioned at the open end of the housing 200 and insert 202. In this embodiment, the window 240 is in the form of a dielectric stand-off and is configured to permit RF energy pulses emitted by the RF emitter 232 to travel therethrough and exit the RF applicator 36.

During operation of the RF applicator 36, the RF emitter 232 of the RF source 230 is conditioned to generate short pulses of RF energy into the partially enclosed space 206 of the insert 202. The housing 200 and insert 202, which function as a waveguide, confine and direct the emitted RF energy pulses so that the RF energy pulses travel along and then out of the RF applicator 36 through the window 240 in the direction indicated by arrow A. Once the RF energy pulses travel out of the RF applicator 36 through the window 210, they are directed into the subject to deliver energy to tissue within the region of interest ROI of the subject S.

During operation the impedance of the RF applicator 36 can be tuned or adjusted in a number of ways. For example, using one or more of the tuning elements 220a, 220b, the RF applicator 36 can be tuned by inserting more or less threaded rod into the partially enclosed space 206 of the insert 202 to alter the impedance of the waveguide. When a tuning element 220a, 220b is adjusted such that only a small amount of its threaded rod extends into the partially enclosed space 206, the tuning element 220a, 220b acts as a shunt capacitor. As the tuning element 220a, 220b is adjusted to increase the amount of threaded rod that extends into the partially enclosed space 206, the capacitance increases. When the tuning element 220a, 220b has been adjusted such that the amount of threaded rod that extends into the partially enclosed space 206 is greater than one-quarter of the wavelength within the waveguide defined by the housing 200 and insert 202, the tuning element 220a, 220b resonates equivalent to a series LC circuit. Further increasing the amount of threaded rod that extends into the partially enclosed space 206 of the insert 202 causes the impedance to change from capacitive to inductive.

Alternatively or in addition to, the impedance of the RF applicator 36 can be tuned or adjusted by changing the temperature within the partially enclosed space 206 of the insert 202. In particular, by changing the temperature of the partially enclosed space 206 within the insert 202 using the heating element 214 and temperature sensor 216, the impedance of the RF applicator 36 can be adjusted.

Alternatively or in addition to, the impedance of the RF applicator 36 may be tuned or adjusted by moving the backplane 204 thereby to change the volume of the partially enclosed space 206 of the insert 202. As will be described, adjusting the impedance of the RF applicator 36 can help to enhance energy delivery during thermoacoustic imaging.

Thermoacoustic imaging can be used to contrast fat or fatty tissues with soft or lean tissues due to their lower electrical conductivity and permittivity in RF compared to other water and ion-rich soft or lean tissues. Fat and fatty tissues also have a lower absorption coefficient compared to soft or lean tissues like muscle. As such, during thermoacoustic imaging of a region of interest that includes a boundary between fat or fatty tissue and soft or lean tissue, bipolar acoustic signals are generated that are received by the thermoacoustic transducer 32. This is due to the fact that the soft or lean tissue absorbs more heat than the fat or fatty tissue causing it to expand rapidly across the boundary and into the fat or fatty tissue, that expands less, and then quickly contract. The strength or peak-to-peak values of the bipolar acoustic signals depend on the relative absorption properties of the fat or fatty tissue and the soft or lean tissue. Further details can be found in the following references: "Scanning thermoacoustic tomography in biological tissue" authored by Ku et al., Med. Phys., vol. 27, no. 5, pp. 1195-202, May 2000; "Microwave-induced thermoacoustic imaging model for potential breast cancer detection" authored by Wang et al., IEEE Trans. Biomed. Eng., vol. 59, no. 10, pp. 2782-01, October 2012; and "IT'IS Database for thermal and electromagnetic parameters of biological tissues" authored by Hasgall et al. Version 3.0, September 2015.

The strengths or peak-to-peak values of the bipolar acoustic signals are proportional to characteristics of the tissue and the delivered RF energy. When the position of the RF applicator 36 is fixed, the delivered RF energy becomes the main source for any change in the strength or peak-to-peak values of the bipolar acoustic signals. As such, adjusting or tuning the impedance of the RF applicator 36 will change the strengths or peak-to-peak values of the bipolar acoustic signals. While monitoring the bipolar acoustic signals, the impedance of the RF applicator 36 can be tuned or adjusted to maximize the strengths or peak-to-peak values of the bipolar acoustic signals. As will be described, the impedance of the RF applicator 36 used to generate the maximum strengths or peak-to-peak values of the bipolar acoustic signals can be readily determined and used to estimate the fractional fat content of the object of interest.

Figure 4:
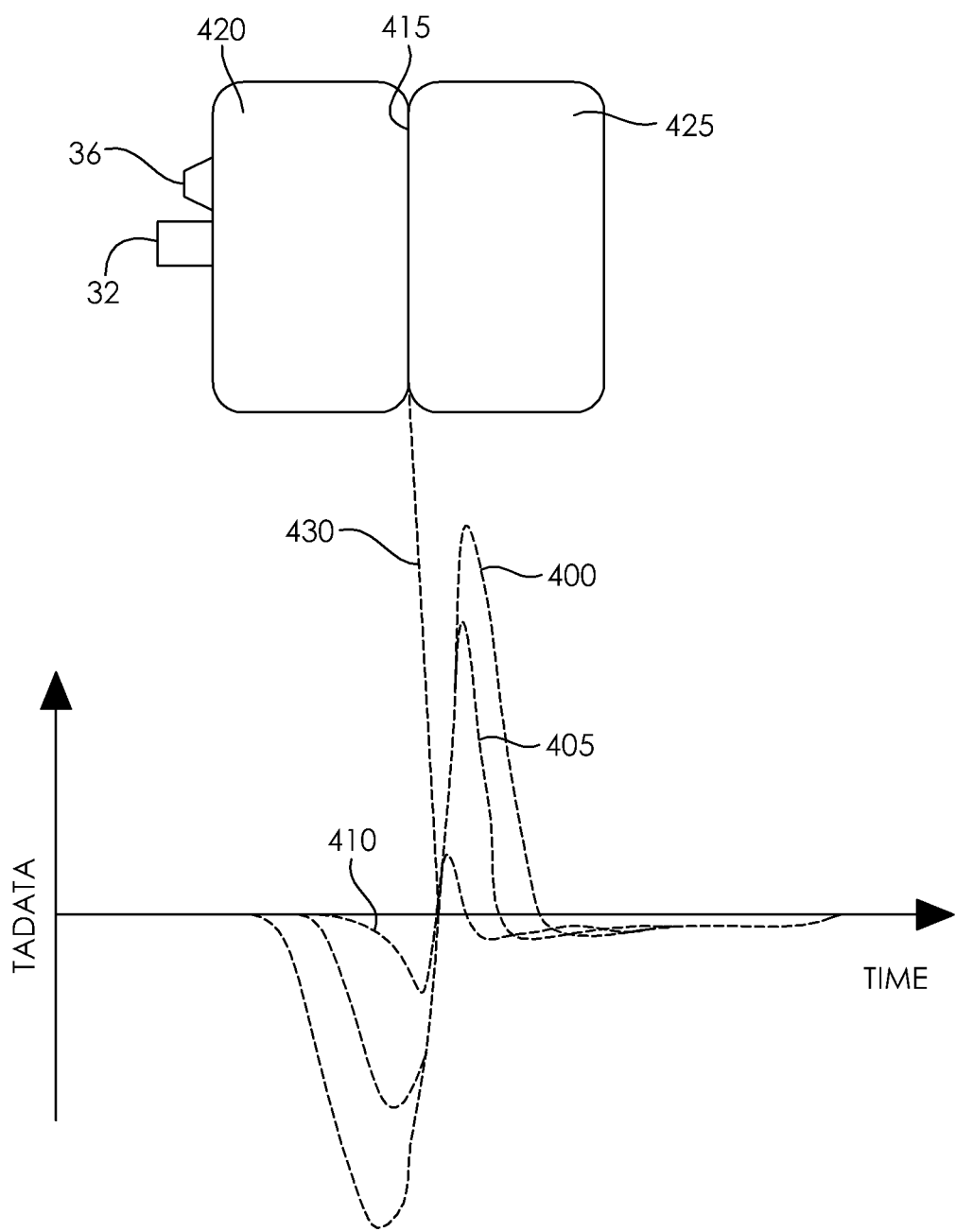
FIG. 4 is a graph showing exemplary bipolar signals.

Exemplary bipolar acoustic signals 400, 405 and 410 are shown in FIG. 4. The bipolar acoustic signals 400, 405 and 410 are generated in response to thermoacoustic imaging of a region of interest ROI comprising a first tissue 420 and a different type of second tissue 425 that are separated by a boundary 415. The dashed line 430 indicates a time point corresponding to the boundary 415. The peak-to-peak amplitude of each bipolar acoustic signal 400, 405 and 410 is proportional to a difference in the absorption coefficients of the first tissue 420 and second tissue 425. In FIG. 4, the first tissue 420 is a kidney and has no fat. For bipolar acoustic signal 400, the second tissue 425 is a fatty liver that has a high fractional fat content. For bipolar acoustic signal 405, the second tissue 425 is an unhealthy liver that has a medium fractional fat content. For bipolar acoustic signal 410, the second tissue 425 is a healthy liver that has a low fractional fat content. As can be seen, the peak-to-peak value of bipolar acoustic signal 400 is greater than that of bipolar acoustic signals 405, 410 and the peak-to-peak value of bipolar acoustic signal 405 is greater than that of bipolar acoustic signal 410. The differences in the peak-to-peak values of the bipolar acoustic signals 400, 405 and 410 represent the extent to which the first tissue 420 expands into the boundary 415 and into the second tissue 425 before contracting.

Different tissues have characteristic dielectric properties at particular frequencies. The dielectric properties determine how much energy is absorbed by tissue. When RF energy pulses are transmitted through tissue, the RF energy pulses are attenuated. The amount of attenuation can be determined using the dielectric properties of the tissue and the physical properties of the tissue. Fatty tissue absorbs less energy than lean tissue. As such, fatty tissue attenuates the RF energy pulses less than normal tissue. Using these properties, the amount of attenuation of tissue can be estimated and this may be used to determine how much fat is in the tissue. Further details can be found in the reference "Determination of added fat in meat paste using microwave and millimetre wave techniques," authored by Ng et al., Meat Science, vol. 79, no. 4, pp. 748-756, August 2008. As such, adjusting the frequency of the RF energy pulses emitted by the RF applicator 36 can help to enhance energy delivery during thermoacoustic imaging.

Figure 5:
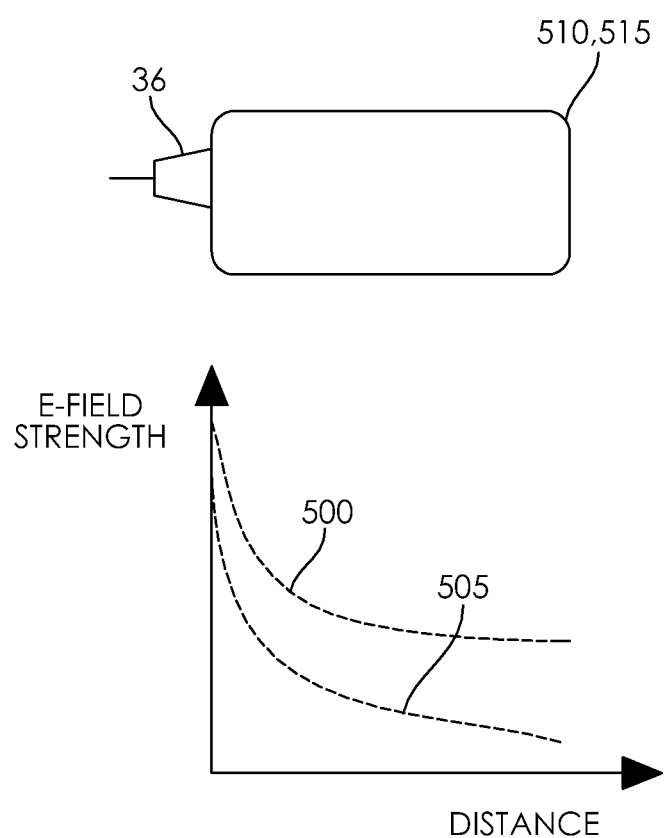
FIG. 5 is a graph showing exemplary electric field strength attenuation curves.

Exemplary electric field strength attenuation curves 500 and 505 are shown in FIG. 5. Each electric field strength attenuation curve 500, 505 represents the electric field strength attenuation of tissue 510, 515, respectively, as a function of distance from the RF applicator 36 of the thermoacoustic imaging system 26. The tissue 510 associated with electric field strength attenuation curve 500 has a higher fat concentration than the tissue 515 associated with electric field strength attenuation curve 505.

Figure 6:
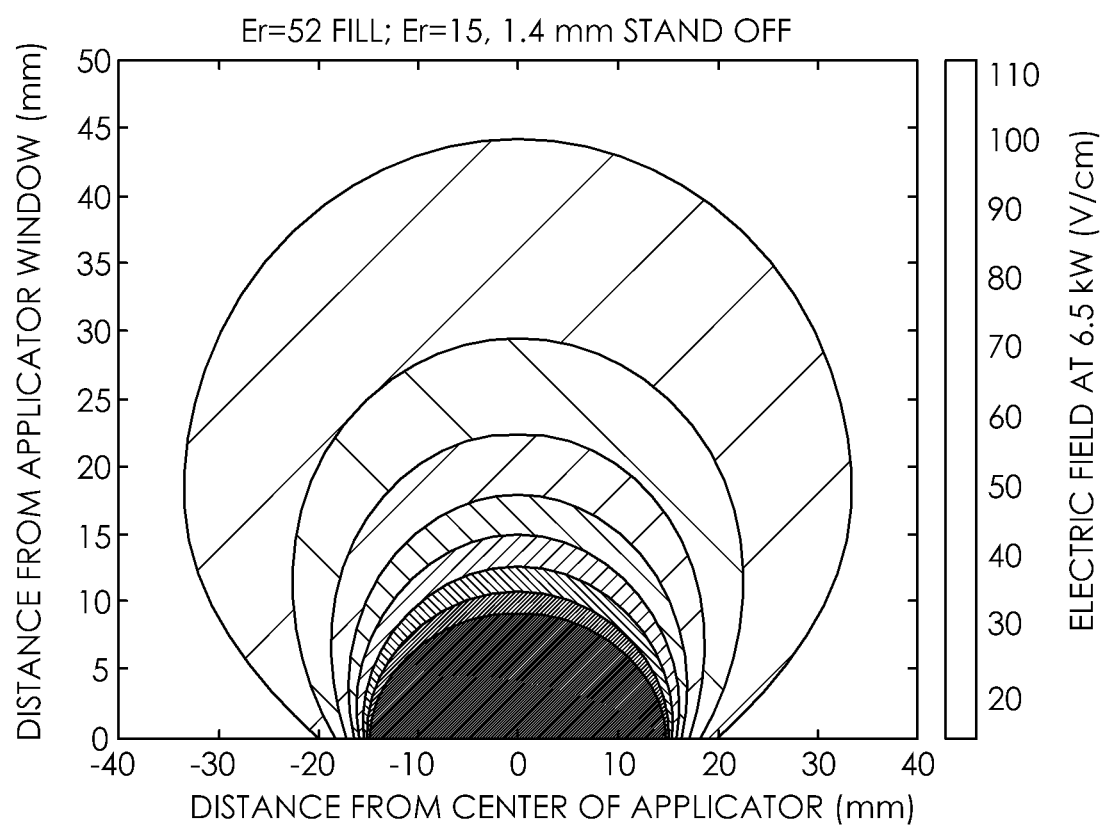
FIG. 6 is a graph showing exemplary flux (energy gradient) of the RF energy pulses emitted by the RF applicator of FIG. 2.

FIG. 6 shows the flux (energy gradient) of an RF energy pulse generated by the RF applicator 36 as it exits the waveguide defined by the housing 200 and insert 202. The window 240 is located and centered at the 0 value of the x-axis. As can be seen, as the distance from the center of the RF applicator 36 increases, the electric field strength decreases. As such, adjusting the distance between the RF applicator 36 and the tissue can help to enhance energy delivery during thermoacoustic imaging.

The imaging system 20 exploits the relationship between the energy absorbing characteristics of the different types of tissue being imaged and the adjustability of the impedance of the RF applicator 36 to estimate fractional fat content of an object of interest.

Figure 7:
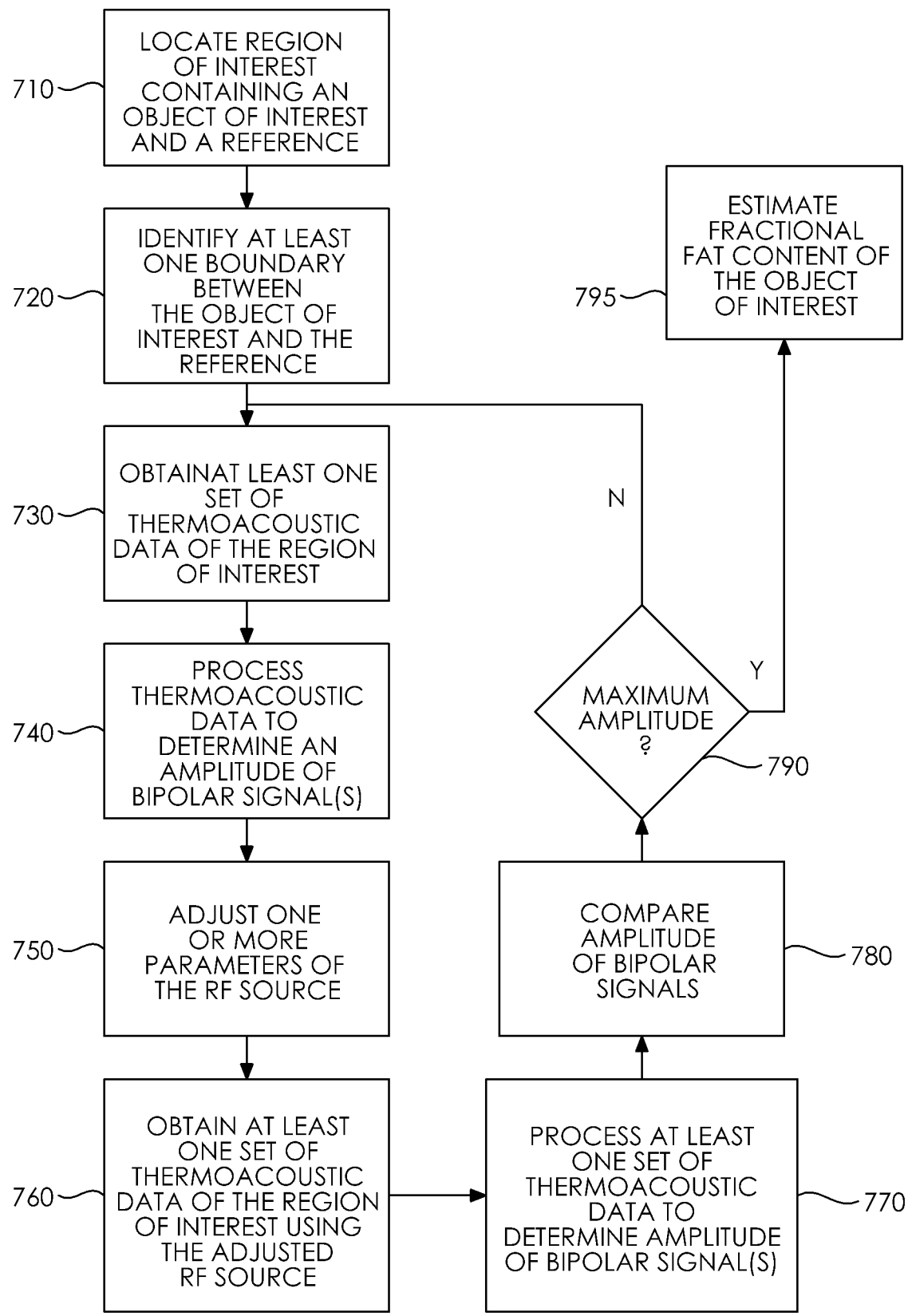
FIG. 7 is a flow chart of a method for estimating the fractional fat content of an object of interest.

Turning now to FIG. 7, a method 700 of estimating fractional fat content of an object of interest is shown. Initially during the method 700, a region of interest ROI within the subject S to be imaged that contains an object of interest and a reference separated by at least one boundary is located (step 710). In this embodiment, the region of interest ROI is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the ultrasound transducer 28 on the subject's body until the region of interest is located. When locating the region of interest, the computing device 22 overlays information associated with the angle of the centerline of the one or more transducer arrays 30 of the ultrasound transducer 28 overtop of the reconstructed ultrasound image on the display device. The information is used to provide feedback to the operator to ensure the axial axis of the ultrasound transducer 28 is generally perpendicular to a boundary between the object of interest and the reference.

Figure 8:
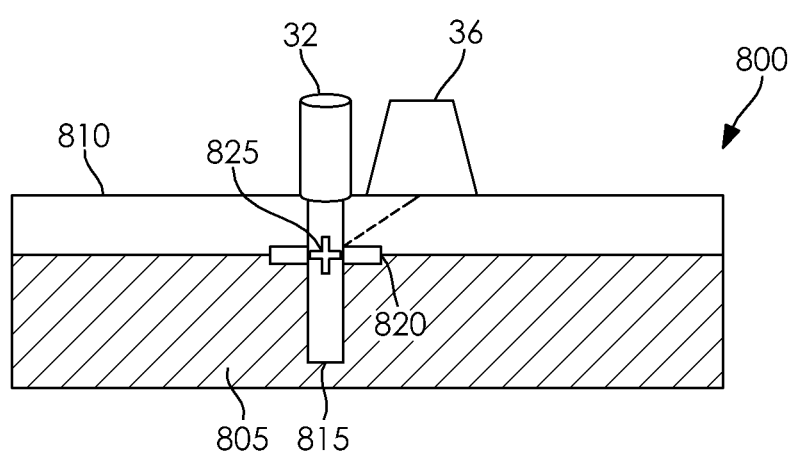
FIG. 8 is an exemplary region of interest containing an object of interest and a reference.

An exemplary region of interest 800 containing an object of interest 805 and a reference 810 is shown in FIG. 8. In this embodiment, the object of interest 805 is the subject's liver and the reference 810 is the subject's kidney. Also shown in FIG. 8 is the RF applicator 36 and the thermoacoustic transducer 32.

At least one boundary between the object of interest and the reference is then identified in the reconstructed ultrasound image (step 720). In this embodiment, the at least one boundary is identified by the operator using an input device such as a mouse coupled to the computing device 22. Specifically, the operator draws a box that encompasses at least a portion of the object of interest 805, at least a portion of the reference 810 and the identified boundary between the portions of the object of interest and the reference. The computing device 22 provides feedback to the operator via the display device to indicate the approximate angle between the box and the boundary to ensure the box is generally perpendicular to the boundary.

An exemplary box 815 is shown in FIG. 8. As can be seen, the box 815 encompasses a portion of the object of interest 805 (the liver), a portion of the reference 810 (the kidney), and the boundary 820 between the object of interest 805 and the reference 810. The boundary 820 is selected at a particular location 825 where the liver and the kidney are in close relation to one another.

As described previously, the RF applicator 36 is conditioned to generate short RF energy pulses. The RF energy pulses travel out of the waveguide defined by the housing 200 and insert 202, through the window 240, and are directed into the region of interest 800 to deliver energy to the object of interest 805 and the reference 810 within the region of interest ROI. In response, bipolar acoustic signals are generated that are detected by the thermoacoustic transducer 32 (step 730).

Since the angle α between the centerline of the one or more transducer arrays 30 of the ultrasound transducer 28 and the centerline of the one or more transducer arrays 34 of the thermoacoustic transducer 32 is known, the operator is able to adjust position of the thermoacoustic transducer 32 with respect to the subject's body such that the thermoacoustic imaging system 26 is able to obtain thermoacoustic image data of the region of interest at a desired imaging angle σ. The desired imaging angle σ is such that the centerline of the one or more transducer arrays 34 of the thermoacoustic transducer 32 extends through the boundary 820 between the object of interest 805 and the reference 810.

Figure 9:
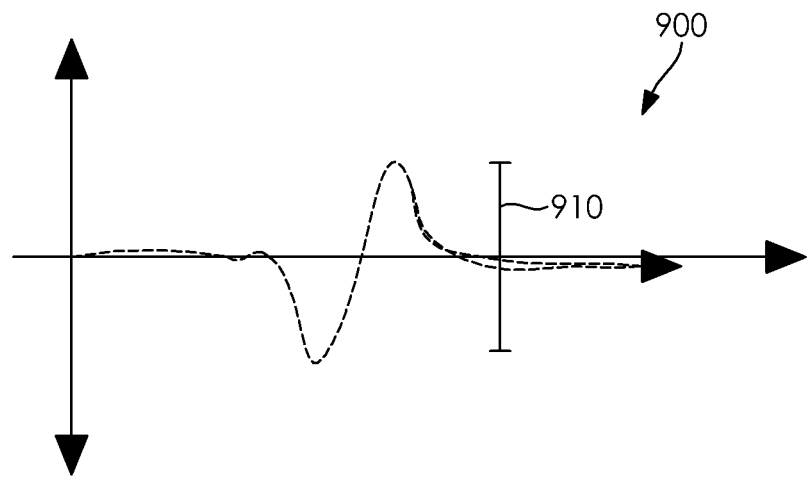
FIGS. 9 to 11 are exemplary bipolar signals obtained according to the method of FIG. 7.

The bipolar acoustic signals are in turn communicated to the computing device 22 for processing (step 740). The computing device 22 is programmed to determine at least one metric of the bipolar acoustic signals. In this embodiment, the metric is the peak-to-peak amplitudes of the bipolar acoustic signals. An exemplary bipolar acoustic signal 900 is shown in FIG. 9. As can be seen, the bipolar acoustic signal 900 comprises a peak-to-peak amplitude 910.

The RF applicator 36 is then adjusted to alter the impedance thereof (step 750). In this embodiment, the impedance of the RF applicator 36 may be adjusted by rotating one or both of the tuning elements 220a and 220b, changing the volume of the partially enclosed space 206 of the insert 202 by moving the backplane 204, and/or by increasing or decreasing the temperature within the partially enclosed space 206 of the insert 202.

Figure 10:
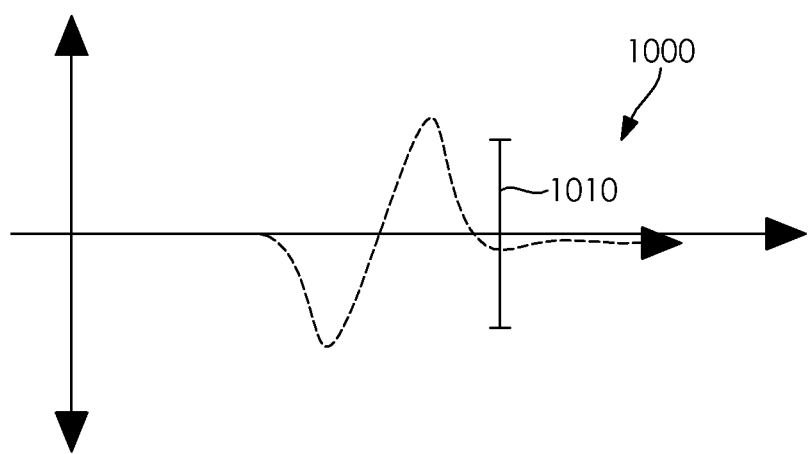

Following the RF applicator adjustment, the RF applicator 30 is again conditioned to generate short RF energy pulses that are directed into the region of interest 800 to deliver energy to the object of interest 805 and the reference 810 (step 760). The resultant bipolar acoustic signals that are generated in the tissue of the region of interest and received by the thermoacoustic transducer 32 are again communicated to the computing device 22 for processing to determine the peak-to-peak amplitudes of the bipolar acoustic signals (step 770). The computing device 22 then compares the peak-to-peak amplitudes of the bipolar acoustic signals with those determined at step 740 to determine if there has been an increase in the peak-to-peak amplitudes (step 780). FIG. 10 shows an exemplary bipolar signal 1000 comprising a peak-to-peak amplitude 1010 that is greater that the peak-to-peak amplitude 910 of bipolar signal 900 (shown in FIG. 9).

Figure 11:
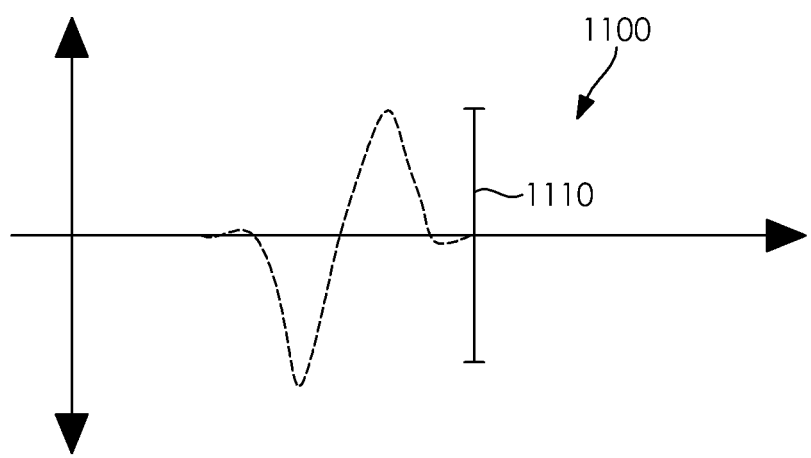

If there is an increase in the peak-to-peak amplitudes, the process reverts back to step 730 and steps 730 to 770 are re-preformed. These steps are preformed iteratively until acoustic bipolar signals having maximum peak-to-peak amplitudes are determined (step 790). FIG. 11 shows an exemplary bipolar acoustic signal 1100 having a maximum peak-to-peak amplitude 1110. As can be seen, the peak-to-peak amplitude 1110 is greater than peak-to-peak amplitude 910 (FIG. 9) and peak-to-peak amplitude 1010 (FIG. 10).

When the RF applicator 36 has been adjusted to maximize the peak-to-peak amplitudes of the generated bipolar acoustic signals, the impedance of the RF applicator 36 is determined. In this embodiment, the impedance of the RF applicator 36 is determined using a network analyzer. The impedance of the RF applicator 36 used to maximize the peak-to-peak amplitudes of the generated bipolar acoustic signals, is used to estimate the fractional fat content of the object of interest (step 795). In this embodiment, a lookup table comparing impedance of the RF applicator 36 used to maximize bipolar acoustic signals to fractional fat content is used. As will be appreciated, the lookup table is generated based on experiments and/or simulations conducted prior to the execution of method 700. Specifically, the lookup table is generated by investigating and tabulating impedances used to maximize the peak-to-peak amplitudes of bipolar acoustic signals for various subcutaneous fat/muscle layer thicknesses and fractional fat contents.

Although in embodiments described above, the at least one metric is described as being the peak-to-peak amplitudes of the bipolar acoustic signals and the method comprises maximizing the peak-to-peak amplitudes, those skilled in the art will appreciate that alternatives are available. For example the at least one metric may be maximum positive or negative amplitudes of the bipolar acoustic signals. As another example, the at least one metric may be the envelope of bipolar acoustic signal. The metric of the bipolar acoustic signals may be maximized and/or enhanced.

Figure 12:
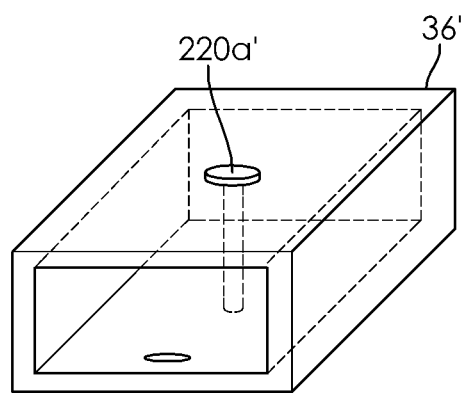
FIG. 12 is another embodiment of an RF applicator.

Turning now to FIG. 12, another embodiment of an RF applicator 36' is shown. RF applicator 36' is generally similar to RF applicator 36 with the following exceptions.

In this embodiment, the RF applicator 36' comprises a single tuning element 220a'. Tuning element 220a' is adjustable by rotating the respective head of the tuning element in a clockwise or counter-clockwise direction to increase or decrease the extent into which the threaded rod extends into the partially enclosed space 206'. In this embodiment, tuning element 220a' is configured to produce an audible sound, in this case a click noise as it is rotated a particular amount, which in this embodiment is ⅛ of a full rotation or 45 degrees.

Each ⅛ rotation of the tuning element 220a' is associated with a particular change in impedance of the RF applicator 36'. Put another way, each time an audible click is heard during rotation of tuning element 220a', the change in impedance of the RF applicator 36' is known. As such, during operation, the amount of tuning required to maximize the peak-to-peak amplitudes of the generated bipolar signals can easily be tracked. The fractional fat content of the object of interest may be estimated using a lookup table (Table 1) comparing click position to fractional fat content.

TABLE 1

Lookup Table Comparing Click Position to Fractional Fat Content

| Click Position | Fractional Fat Content of the Object of Interest (FFC) |
| --- | --- |
| 1 | FFC ≤ 5% |
| 2 | 5% < FFC ≤ 10% |
| 3 | 10% < FFC ≤ 15% |
| 4 | 15% < FFC ≤ 20% |
| 5 | 20% < FFC ≤ 25% |
| 6 | 25% < FFC ≤ 30% |
| 7 | 35% < FFC ≤ 40% |
| 8 | FFC > 40% |

As will be appreciated, similar to RF applicator 36, the RF applicator 36' may have additional tuning elements. In embodiments, each additional tuning element may be configured to produce an audible sound as it is rotated.

As will be appreciated, the particular amount of rotation required to generate an audible click is not limited to ⅛ rotation. In other embodiments, the particular amount may be another amount, such as for example ¼ rotation, ⅕ rotation, ¹⁄₁₀ rotation, ¹⁄₂₅ rotation, etc.

In another embodiment, each ⅛ rotation of each tuning element 220a' may be associated with a particular change in fractional fat content of the object of interest. For example, each ⅛ rotation of each tuning element 220a' may identify a change in 5% fat of the object of interest. As such, during operation, the fractional fat content of the object of interest can be easily identified.

In another embodiment, alternatively or in addition to the tuning elements being configured to produce an audible click, the threaded rod 208 and nut 210 may be configured to produce an audible click as the threaded rod 208 is rotated. As such, an audible click may be heard when changing the volume of the partially enclosed space 206 of the insert 202 by moving the backplane. This audible click may be used to estimate fractional fat content using a lookup table.

In another embodiment, where the object of interest is a liver, the RF applicator 36' may be calibrated to determine a particular impedance used to maximize the peak-to-peak amplitudes of generated bipolar acoustic signals for a healthy liver. During operation, this particular impedance may be used as starting point. If the subject being imaged does not have a healthy liver, the peak-to-peak amplitudes of the bipolar signals generated would not be maximized. The RF applicator 26' may then be adjusted by rotating the tuning element 220a'. By tracking the amount of audible clicks required to maximize the peak-to-peak amplitudes of the bipolar signals, the fractional fat content of the liver may be estimated. This may be further assisted using a lookup table (Table 2) comparing the amount of audible clicks heard to fractional fat content.

TABLE 2

Lookup Table Comparing Clicks Heard to Fractional Fat Content

| Audible Clicks Heard | Fractional Fat Content of the Object of Interest (FFC) |
| --- | --- |
| 0 | FFC ≤ 5% |
| 1 | 5% < FFC ≤ 10% |
| 2 | 10% < FFC ≤ 15% |
| 3 | 15% < FFC ≤ 20% |
| 4 | 20% < FFC ≤ 25% |
| 5 | 25% < FFC ≤ 30% |
| 6 | 35% < FFC ≤ 40% |
| 7 | FFC > 40% |

Although in embodiments described above the fractional fat content is estimated using the impedance of the RF applicator used to maximize peak-to-peak amplitudes of bipolar acoustic signals, those skilled in the art will appreciate that other factors may be used to estimate the fractional fat content.

For example, in another embodiment, RF forward and reflecting powers may be used. As is known, RF forward power is the power of the RF energy pulses emitted by the RF applicator. RF reflected power is the power of the RF energy pulses that is reflected back to the RF source from the RF applicator. VSWR (Voltage Standing Wave Ratio) is calculated from the RF forward and RF reflected power and is measure of how efficiently RF power is being transmitted from the RF applicator.

In this embodiment, when the RF applicator is placed on a predefined region of the body and fixed inputs and system settings are used, difference in patient conditions, such as for example difference in thickness of fat within the region of interest, results in difference in RF energy delivery. These factors can be used to estimate fractional fat content of the object of interest.

In this embodiment, RF energy pulses are directed through at least one intermediate area and into a region of that comprises the object of interest. The one or more RF energy pulses having a known frequency and a known amplitude. A first power monitor is used to measure the forward power of the RF energy pulses. A second power monitor is used to measure the reflected power of the RF energy pulses. The fractional fat content of the object of interest is estimated based on the measured forward power, the measured reflected power, and an estimated thickness of said at least one intermediate area.

In this embodiment, the VSWR is calculated as a ratio of the measured forward power and the measured reflected power. Using the measured forward power, the VSWR, and the estimated thickness of the at least one intermediate area, the fractional fact content is estimated using a lookup table.

Those skilled in the art will appreciate that other power related measurements may be used.

In another embodiment, the fractional fat content of the object of interest may be estimated using equation 1:

$$FFC = f(P_f, VSWR, d_f, d_m) \quad [1]$$

where FFC denotes the estimated fractional fat content of the object of interest, f is a conversion function, $P_f$ is the forward power, VSWR is the Voltage Standing Wave Ratio, $d_f$ is the thickness of the subcutaneous fat layer, and $d_m$ is the thickness of the muscle layer (up to the liver).

In one embodiment, ultrasound imaging is used to estimate the thicknesses cited in the prior paragraph. For an ultrasound transducer that provides good resolution near the surface (skin), the thicknesses of both subcutaneous fat and muscle will be separately estimated. A linear probe is an example of such an ultrasound transducer. When an ultrasound probe or transducer does not have enough capability to clearly differentiate subcutaneous fat and muscle layers, a combined thickness d=df+dm will be used instead, along with appropriate models.

In embodiments where a network analyzer is used to tune the RF applicator, a data set may be collected during a clinical study where a statistically-significant number of subjects are used to obtain a non-invasive thermoacoustic measurement of the object of interest and a gold standard fractional fat content assessment of that object of interest.

Those skilled in the art will appreciate that in embodiments the computing device 22 may be programmed to adjust parameters of the RF applicator. For example, the computing device may be coupled to one or more actuators configured to adjust the tuning elements 220a, 220b and/or the threaded rod 208.

Those skilled in the art will appreciate that the above-described method may be performed on a phantom designed to mimic an area of interest. In this embodiment, the RF applicator may be adjusted to maximize the peak-to-peak amplitudes of the bipolar acoustic signals prior to imaging a patient. Further, the method may be performed on numerous phantoms of various sizes to mimic different sizes of patients.

Figure 13:
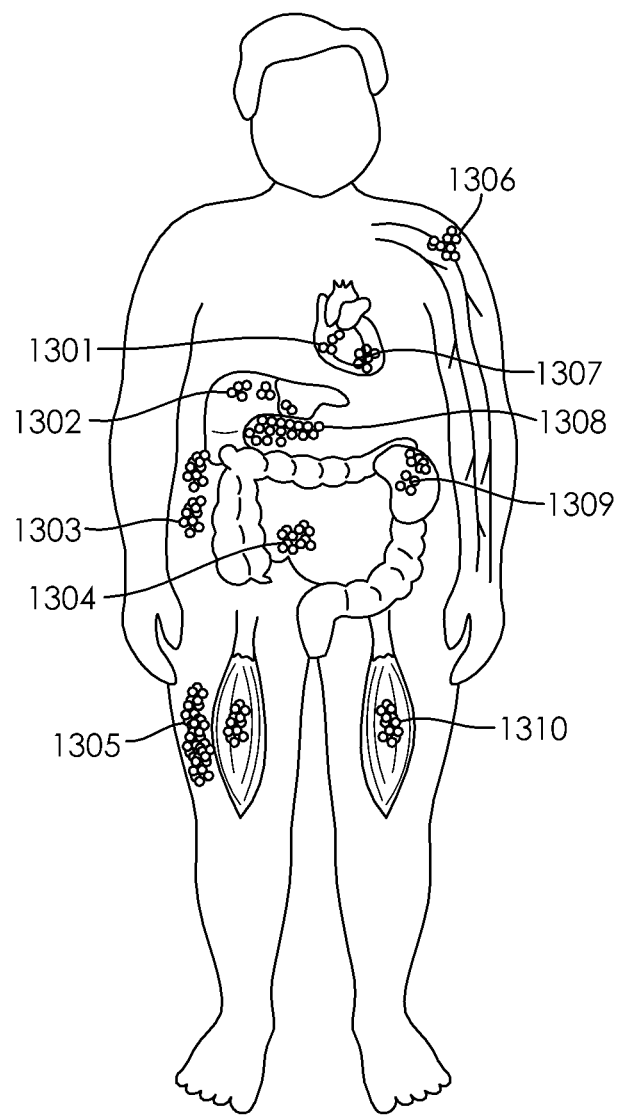
FIG. 13 shows various parts of a human body that can be imaged using the imaging system of FIG. 1 according to the method of FIG. 7.

Although in embodiments the object of interest is described as being the liver and the reference is described as being the kidney, those skilled in the art will appreciate that thermoacoustic data may be obtained for other parts of the body. As shown in FIG. 13, various parts of the body that may be imaged using the above-described system and method include the epi/pericardial adipose tissue 1301, the liver 1302, subcutaneous adipose tissue 1303, visceral adipose tissue 1304, subcutaneous gluteal-femoral adipose tissue 1305, perivascular adipose tissue 1306, myocardial fat 1307, pancreas fat 1308, renal sinus fat 1309, and muscle fat 1310.

In another embodiment, the space enclosed by the insert 202, backplane 204 and the window 240 may be partially or fully-filled with material that conducts RF energy pulses such as for example a liquid, gel, ceramic or putty. As will be appreciated, in this embodiment, the material partially or fully filling the space may be heated or cooled thereby increasing or decreasing the temperature within the insert 202. As such, the frequency of the RF energy pulses may be adjusted.

Although embodiments have been described above with reference to the accompanying drawings, those of skill in the art will appreciate that variations and modifications may be made without departing from the scope thereof as defined by the appended claims.

What is claimed is:

1. A method for estimating fractional fat content of an object of interest, the method comprising:
  (i) directing, using a radio frequency (RF) applicator, one or more RF energy pulses into a region of interest, the region of interest comprising the object of interest and at least one reference that are separated by at least one boundary;
  (ii) detecting, using an acoustic receiver, at least one bipolar acoustic signal generated in the region of interest in response to the RF energy pulses and processing the at least one bipolar acoustic signal to determine a peak-to-peak amplitude thereof;
  (iii) adjusting an impedance of the RF applicator to enhance at least one metric of bipolar acoustic signals generated in the region of interest in response to RF energy pulses generated by the adjusted RF applicator; and
  (iv) estimating fractional fat content of the object of interest based on the adjusted impedance of the RF applicator.

2. The method of claim 1, wherein the at least one metric is at least one of the peak-to-peak amplitude of the bipolar acoustic signals, a maximum amplitude of the bipolar acoustic signals and an envelope of the bipolar acoustic signals.

3. The method of claim 1, wherein adjusting the impedance of the RF applicator to enhance at least one metric of bipolar acoustic signals comprises adjusting the impedance of the RF applicator to maximize the at least one metric of bipolar acoustic signals.

4. The method of claim 1, wherein during step (i), the RF applicator is set at a predefined impedance.

5. The method of claim 4, wherein estimating fractional fat content of the object of interest based on the adjusted impedance of the RF applicator comprises comparing the adjusted impedance to the predefined impedance.

6. The method of claim 1, wherein estimating fractional fat content of the object of interest comprises looking up the adjusted impedance in a lookup table.

7. The method of claim 1, wherein adjusting the impedance of the RF applicator comprises at least one of:
  adjusting a tuning element of the RF applicator;
  adjusting a volume of a waveguide of the RF applicator; and
  adjusting a temperature within the waveguide of the RF applicator.

8. The method of claim 1, wherein the boundary is at a location between at least two different types of tissue.

9. The method of claim 8, wherein the two different types of tissue are one of:
  muscle and fat;
  a blood vessel and fat; and
  liver tissue and kidney tissue.

10. A system for estimating fractional fat content of an object of interest within a region of interest, the system comprising:
  a thermoacoustic imaging system comprising an adjustable radio frequency (RF) applicator configured to emit RF energy pulses into the region of interest and heat tissue therein and an acoustic receiver configured to receive bipolar acoustic signals generated in response to heating of tissue in the region of interest; and one or more processors configured to:
process bipolar acoustic signals received by the acoustic receiver in response to RF energy pulses emitted into the region of interest using the RF applicator to determine a setting for the RF applicator that yields bipolar acoustic signals with at least one enhanced metric thereof;
determine an impedance of the RF applicator used to yield acoustic bipolar signals with the enhanced at least one metric; and
estimate fractional fat content of the object of interest using the determined impedance.

11. The system of claim 10, wherein the at least one metric is at least one of the peak-to-peak amplitude of the bipolar acoustic signals, a maximum amplitude of the bipolar acoustic signals and an envelope of the bipolar acoustic signals.

12. The system of claim 10, wherein the setting for the RF applicator is a setting that yields bipolar acoustic signals with at least one maximum metric thereof.

13. The system of claim 10, wherein the one or more processors are further configured to:
estimate the fractional fat content of the object of interest using a lookup table.

14. The system of claim 10, wherein the adjustable RF applicator comprises at least one tuning element configured to alter the impedance of a waveguide of the RF applicator.

15. The system of claim 14, wherein the at least one tuning element is rotatable to alter an impedance of the waveguide.

16. The system of claim 15, wherein the at least one tuning element produces audible sounds during rotation.

17. The system of claim 16, wherein each audible sound is used to estimate the fractional fat content of the object of interest.

18. The system of claim 10, wherein the adjustable RF applicator comprises a waveguide having an adjustable volume.

19. The system of claim 10, wherein the adjustable RF applicator comprises at least one heating element configured to alter a temperature within a waveguide of the RF applicator.

20. A method for estimating fractional fat content of an object of interest, the method comprising:
(i) directing, using a radio frequency (RF) applicator, one or more RF energy pulses into a region of interest, the region of interest comprising the object of interest and at least one reference that are separated by at least one boundary;
(ii) detecting, using an acoustic receiver, at least one bipolar acoustic signal generated in the region of interest in response to the RF energy pulses and processing the at least one bipolar acoustic signal to determine a peak-to-peak amplitude thereof;
(iii) adjusting an impedance of the RF applicator;
(iv) directing, using the adjusted RF applicator, one or more RF energy pulses into the region of interest;
(v) detecting, using the acoustic receiver, at least one bipolar acoustic signal generated in the region of interest in response to the RF energy pulses generated by the adjusted RF applicator and processing the at least one bipolar acoustic signal to determine a peak-to-peak amplitude thereof;
(vi) comparing the peak-to-peak amplitude determined at step (v) with a previously determined peak-to-peak amplitude;
(v) repeating steps (ii), (iv) and (v) until the peak-to-peak amplitude of the at least bipolar acoustic signal determined at step (v) is maximized and;
(vi) estimating fractional fat content of the object of interest based on the impedance of the RF applicator used to maximize the bipolar acoustic signal.

* * * * *